United States Patent
Kuo et al.

(10) Patent No.: US 9,029,522 B2
(45) Date of Patent: May 12, 2015

(54) RECOMBINANT FUSION INTERFERON FOR ANIMALS

(71) Applicant: SBC Virbac Biotech Co., Ltd., Taipei (TW)

(72) Inventors: Tsun-Yung Kuo, I-Lan (TW); Chung-Chin Wu, I-Lan County (TW); Han-Ting Chen, Taoyuan County (TW)

(73) Assignee: SBC Virbac Biotech Co., Ltd., Taipei (TW)

( * ) Notice: Subject to any disclaimer, the term of this patent is extended or adjusted under 35 U.S.C. 154(b) by 0 days.

(21) Appl. No.: 14/306,808

(22) Filed: Jun. 17, 2014

(65) Prior Publication Data

US 2014/0308706 A1  Oct. 16, 2014

Related U.S. Application Data

(62) Division of application No. 13/557,139, filed on Jul. 24, 2012, now Pat. No. 8,784,834.

(51) Int. Cl.
| | | |
|---|---|---|
| *C07H 21/04* | (2006.01) |
| *C12P 21/06* | (2006.01) |
| *C12P 21/04* | (2006.01) |
| *C07K 14/555* | (2006.01) |
| *C07K 14/56* | (2006.01) |
| *C07K 19/00* | (2006.01) |

(52) U.S. Cl.
CPC .............. *C07K 14/555* (2013.01); *C07K 14/56* (2013.01); *C07K 19/00* (2013.01); *C07K 2319/30* (2013.01)

(58) Field of Classification Search
None
See application file for complete search history.

(56) References Cited

U.S. PATENT DOCUMENTS

2002/0081664 A1* 6/2002 Lo et al. ................... 435/69.5

OTHER PUBLICATIONS

Kacskovics et al. (1994), The Journal of Immunology, vol. 153, p. 3565-3573.*
Cheng et al. (2006), Gene 382, vol. 282, p. 28-38.*

* cited by examiner

*Primary Examiner* — Christine J Saoud
*Assistant Examiner* — Jegatheesan Seharaseyon
(74) *Attorney, Agent, or Firm* — Tim Tingkang Xia, Esq.; Morris, Manning & Martin, LLP

(57) ABSTRACT

A recombinant fusion interferon for animals. The recombinant fusion interferon comprises an animal interferon and a Fc region of an animal immunoglobulin G (IgG). The animal interferon and the Fc region of the animal immunoglobulin G can be further joined by a linker. A polynucleotide that encodes the recombinant fusion interferon for animals, a method for producing the recombinant fusion interferon, and the use of the recombinant fusion interferon.

5 Claims, 3 Drawing Sheets

RECOMBINANT FUSION INTERFERON FOR ANIMALS

RELATED APPLICATIONS

This application is a divisional application of U.S. patent application Ser. No. 13/557,139, filed Jul. 24, 2012. The entirety of the above-mentioned patent application is hereby incorporated by reference herein and made a part of specification.

BACKGROUND OF THE INVENTION

1. Field of the Invention

The present invention relates to a recombinant fusion interferon for animals, particularly to a recombinant fusion interferon having antiviral activities against animal viruses.

2. Description of the Related Art

Interferon (IFN) is initially discovered in 1957 by Alick Isaacs and Jean Lindenmann during research of influenza virus. After infected by virus, the host cells immediately secrete a cytokine to induce other cells nearby to produce antiviral proteins to interfere with viral replication. This cytokine is later named IFN. Since the first discovery of IFN, three types of IFN have been identified—type I IFN (IFN-α and IFN-β), type II IFN (IFN-γ), and type III IFN (IFN-λ). The antiviral effects of IFN are mainly provided by type I IFN (IFN-α and IFN-β). In addition to antiviral activities, IFN has anti-tumor activity, and can induce cell differentiation and modulate immune response.

So far, the majority of commercial IFN is used for the treatment of human diseases, such as human hepatitis B, human hepatitis C, Kaposi's sarcoma (KS), and malignant melanoma.

Without an effective vaccine for preventing an animal virus, an infected animal of the virus can only be treated with supportive therapy. However, supportive therapy is usually ineffective, and therefore the infection of animal virus may cause great economic losses in livestock husbandry.

Therefore, it is important to develop IFN having antiviral activities against animal viruses.

SUMMARY OF THE INVENTION

The first aspect of the present invention relates to a recombinant fusion IFN for animals. IFN possesses a short serum half-life (about 2 to 8 hours) due to its small molecular size. In one embodiment, the present invention provides a stably recombinant fusion IFN for animals in which an animal IFN is fused with an animal IgG Fc possessing a long serum half-life. The animal IgG Fc is fused with the N-terminus or the C-terminus of the animal IFN.

In one preferred embodiment, the animal IFN and the animal IgG Fc are joined by a peptide linker comprising glycine and serine residues. In another embodiment, the animal IFN is a porcine IFN α. The porcine IFN α encodes an amino acid sequence of SEQ ID No. 2. In yet another embodiment, the animal IgG Fc is a porcine immunoglobulin Fc fragment. The porcine IgG Fc encodes an amino acid sequence of SEQ ID No. 4.

In still another embodiment, the peptide linker encodes an amino acid sequence of SEQ ID No. 6.

In a further embodiment, the recombinant fusion IFN for animals encodes an amino acid sequence of SEQ ID Nos. 8 or 10.

The second aspect of the present invention relates to a polynucleotide encoding the recombinant fusion IFN for animals of the present invention. A DNA sequence encoding an animal IFN and a DNA sequence encoding an animal IgG Fc are cloned into an expression vector to obtain the polynucleotide encoding the recombinant fusion IFN for animals. The vector containing the polynucleotide encoding the recombinant fusion IFN for animals is then introduced to a host cell where the recombinant fusion IFN for animals can be expressed.

In one preferred embodiment, in addition to clone a DNA sequence encoding an animal IFN and a DNA sequence encoding an animal IgG Fc into an expression vector, a DNA sequence encoding a peptide linker having glycine and serine residues is further cloned into the expression vector to join the DNA sequence encoding an animal IFN and the DNA sequence encoding an animal IgG Fc.

In another embodiment, the DNA sequence encoding an animal IFN comprises SEQ ID No. 1.

In yet another embodiment, the DNA sequence encoding an animal IgG Fc comprises SEQ ID No. 3.

In still another embodiment, the DNA sequence encoding a peptide linker comprises SEQ ID No. 5.

In a further embodiment, the polynucleotide encoding the recombinant fusion IFN for animals comprises SEQ ID No. 7.

The expression vector can be a prokaryotic expression vector or a eukaryotic expression vector. The prokaryotic expression vector includes, but is not limited to, pET, pGEX, and pDEST expression vectors. The eukaryotic expression vector includes, but is not limited to, pSecTag, pcDNA3, pCMV-Script, pCI, and pSV40b expression vectors.

The host cell can be a prokaryotic cell, such as bacteria, or a eukaryotic cell, such as yeast, insect cells, plant cells, and mammalian cells. In one embodiment, the host cell is *Escherichia coli* (*E. coli*). In another embodiment, the host cell is a mammalian cell. The mammalian cells that can be used to express the recombinant fusion IFN for animals of the present invention include, but are not limited to, 3T3 cells, Chinese hamster ovary cells (CHO cells), baby hamster kidney cells (BHK cells), human cervical cancer cells (such as Hela cells), and human liver carcinoma cells (such as HepG2 cells).

Since codon usage bias is common in both prokaryotes and eukaryotes, the DNA sequence encoding an animal IFN and the DNA sequence encoding an animal IgG Fc according to embodiments of the present invention may be adjusted to the codon usage of abundant proteins in the eukaryotic host cells, such that optimized protein expression level in the eukaryotic host cells without changing the amino acid sequences of the animal IFN and the animal IgG Fc fragment may be achieved.

In one embodiment, the modified polynucleotide of the recombinant fusion IFN for animals comprises SEQ ID No. 9, which encodes the amino acid sequence of SEQ ID No. 8.

The third aspect of the present invention relates to an optimized method for producing the recombinant fusion IFN for animals in mammalian host cells.

In one embodiment, the method comprises the steps of (1) cultivating mammalian host cells having a polynucleotide encoding the recombinant fusion IFN for animals of the present invention in serum-containing medium, (2) replacing the serum-containing medium with serum-free medium after the cells grow stably, (3) collecting the serum-free medium, which contains the recombinant fusion IFN for animals of the present invention, and adding new serum-free medium to the cells every 1 to 5 days.

The mammalian host cells include, but are not limited to, 3T3 cells, CHO cells, BHK cells, human cervical cancer cells (such as Hela cells), and human liver carcinoma cells (such as HepG2 cells). In one embodiment, the mammalian host cells are CHO cells.

The serum includes, but is not limited to, bovine serum and horse serum. In one embodiment, the serum is fetal bovine serum (FBS).

The content of serum in the medium is about 0.1 to 10% (v/v). In one embodiment, the content of serum is 5% (v/v).

The fourth aspect of the present invention relates to a composition comprising the recombinant fusion IFN for animals of the present invention and a pharmaceutically acceptable excipient.

The excipient may be pharmaceutically acceptable organic or inorganic carrier substances suitable for parenteral, enteral or intranasal application which do not deleteriously react with the active compounds and are not deleterious to the recipient thereof. Suitable excipients include, but are not limited to, water, salt solutions, vegetable oils, polyethylene glycols, gelatin, lactose, amylose, magnesium stearate, talc, silicic acid, viscous paraffin, fatty acid monoglycerides and diglycerides, petroethral fatty acid esters, hydroxymethyl-cellulose, polyvinylpyrrolidone, etc. In one embodiment, the excipient is phosphate buffer solution (PBS).

The fifth aspect of the present invention relates to a method for treating or inhibiting virus infection in an animal. In one embodiment, the method comprises administering a composition comprising the recombinant fusion IFN for animals of the present invention to an animal. The virus may be an animal DNA virus or an animal RNA virus. The animal DNA virus includes, but is not limited to, pseudorabies virus, (PRV). The animal RNA virus includes, but is not limited to, porcine reproductive and respiratory syndrome virus (PRRSV). The animal may be an animal infected with an animal virus or an animal not infected with an animal virus. In another embodiment, the composition further comprises a pharmaceutically acceptable excipient.

These and other aspects of the present invention will become apparent from the following description of the preferred embodiment taken in conjunction with the following drawings, although variations and modifications therein may be effected without departing from the spirit and scope of the novel concepts of the disclosure.

BRIEF DESCRIPTION OF THE DRAWINGS

The accompanying drawings illustrate one or more embodiments of the invention and together with the written description, serve to explain the principles of the invention. Wherever possible, the same reference numbers are used throughout the drawings to refer to the same or like elements of an embodiment, and wherein.

DETAILED DESCRIPTION OF THE PREFERRED EMBODIMENT

Figure 1:
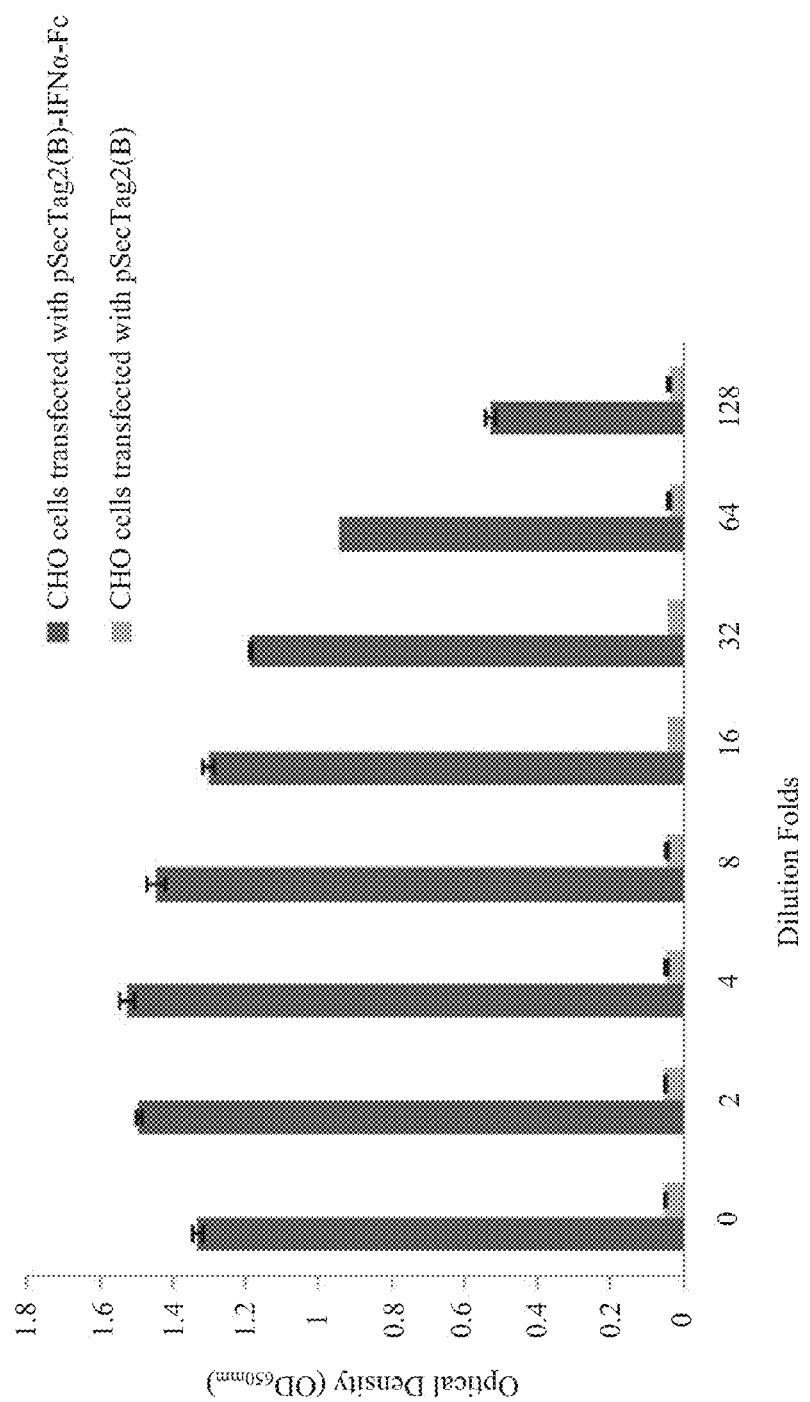
FIG. 1 shows an enzyme-linked immunosorbent assay (ELISA) assay of CHO cells that was transfected with a plasmid containing a DNA sequence encoding the recombinant fusion IFN for animals according to one embodiment of the present invention and then screened by zeocin and CHO cells that was transfected with pSecTag2(B) and then screened by zeocin.

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views.

As used in the description herein and throughout the claims that follow, the meaning of "a", "an", and "the" includes plural reference unless the context clearly dictates otherwise. Moreover, titles or subtitles may be used in the specification for the convenience of a reader, which shall have no influence on the scope of the present invention.

The terms "treat," "treating," "treatment," and the like are used herein to refer to prevention or partially preventing a disease, symptom, or condition and/or a partial or complete cure or relief of a disease, condition, symptom, or adverse effect attributed to the disease. Thus, the terms "treat," "treating," "treatment," and the like refer to both prophylactic and therapeutic treatment regimes.

The terms "inhibit," "inhibiting," "inhibition," and the like are used herein to refer to a reduction or decrease in a quality or quantity, compared to a baseline. For example, in the context of the present invention, inhibition of viral replication refers to a decrease in viral replication as compared to baseline. Similarly, inhibiting virus infection refers to a decrease in virus infection as compared to baseline.

The term "antiviral activity" is used herein to refer to that the IFN can inhibit or interfere the biological activity of virus.

The term "biological activity of virus" is used herein to refer to virus infection, replication, and the like.

The meaning of the technical and scientific terms as described herein can be clearly understood by a person of ordinary skill in the art.

EXAMPLE 1

Molecular Cloning of Porcine IFN α (P IFNα)

Peripheral blood mononuclear cells (PBMCs) were firstly isolated from blood of a pig (L×Y-D strain). A total RNA was isolated from the PBMCs by the guanidine thiocyanate (GTC) method and then was used in a reverse transcription polymerase chain reaction (RT-PCR) to generate complementary DNA (cDNA). Briefly, 20 μl of total RNA was incubated at 70° C. for 3 minutes, and after incubation, 10 μl of 5× buffer, 8 μl of 1.25 mM dNTP, 1 μl of oligo dT primers, 11 μl of diethyl pyrocarbonate (DEPC)-treated water, 0.5 μl of RNasin® RNase inhibitor, and 0.5 μl of Avian Myeloblastosis Virus (AMV) reverse transcriptase were added and incubated at 42° C. for 30 minutes to synthesize cDNA. The cDNA was then used as DNA template to amplify porcine IFN α gene by polymerase chain reaction (PCR). A forward primer and a reverse primer were designed to amplify the P IFNα nucleotide sequence. The forward primer in this example has a HindIII cleavage site, and the reverse primer in this example has an Xho I cleavage site. A PCR mixture containing 10 μl of cDNA, 5 μl of 10×PCR buffer, 8 μl of 1.25 mM dNTP, 1 μl of forward primer, 1 µl of reverse primer, 24 µl autoclaved water, and 1 µl of Taq polymerase were placed in a GeneAmp® PCR System 2400 reactor (Applied Biosystems). After inactivating the cDNA at 95° C. for 5 minutes, the DNA encoding P IFNα was amplified by Taq polymerase with 30 cycles of 95° C. for 1 minute, 55° C. for 30 seconds, 72° C. for 30 seconds, and followed by a final extension at 72° C. for 5 minutes. The primers for cloning P IFNα are the following:

```
Forward primer (IFN-F1):
                                    (SEQ ID NO: 11)
5'-CCCAAGCTTATGGCCCCAACCTCAGCC-3'
      HindIII Reverse primer (IFN-R1):
                                    (SEQ ID NO: 12)
5'-CCGCTCGAGCAGGTTTCTGGAGGAAGA-3'
      XhoI
```

The sizes of PCR products were detected by agarose electrophoresis. Then, the PCR products were purified with a DNA purification kit (Protech Technology Enterprise, Taiwan). After purification, the PCR products were constructed into a pET20b expression vector. The purified PCR products and pET20b expression vector (Novagen) were digested with two restriction enzymes, Hind III and Xho I (New England Biolabs), respectively for 8 hours at 37° C. After restriction enzyme cleavage reaction, the digested PCR products and pET20b expression vector were purified with a DNA purification kit (Protech Technology Enterprise, Taiwan) respectively. The purified PCR products were ligated with the purified pET20b expression vector, and the ligation product was transformed into host cells (*E. coli*). Transformants were selected, and DNA sequence was confirmed by DNA sequencing. The porcine IFN α (P IFNα) has a DNA sequence of SEQ ID No. 1 and an amino acid sequence of SEQ ID No. 2. The plasmid containing the DNA sequence of the porcine IFN α (P IFNα) is named pET20b-IFNα.

EXAMPLE 2

Molecular Cloning of Porcine Immunoglobulin Fc Fragment

Porcine immunoglobulin Fc fragment (P IgG Fc) was cloned from the total RNA preparation of pig spleen by RT-PCR and PCR methods described in Example 1. The primers for cloning the P IgG Fc are the following:

```
Forward primer (IgG-F1):
                                    (SEQ ID NO: 13)
5'-CGGGATCCGGGAACAAAGACC-3'
      BamHI Reverse primer (IgG-R):
                                    (SEQ ID NO: 14)
5'-CCCAAGCTTTTTACCCGGAGTC-3'
      HindIII
```

A BamHI site at the 5' end and a HindIII site at the 3' end of the P IgG Fc were created by PCR. The PCR products were gel-purified and subcloned into pET20b expression vectors by the methods described in Example 1. Then DNA sequence was confirmed by sequencing. The P IgG Fc has a DNA sequence of SEQ ID No. 3 and an amino acid sequence of SEQ ID No. 4. The plasmid containing the DNA sequence of the P IgG Fc is named pET20b-IgG-Fc.

EXAMPLE 3

Construction of Vector Containing Polynucleotide Sequence Encoding Porcine Recombinant Fusion IFN (P IFN-Fc)

The DNA sequence of porcine IFNα (P IFNα) cloned in Example 1 (SEQ ID No. 1) and the DNA sequence of porcine immunoglobulin Fc fragment (P IgG Fc) cloned in Example 2 (SEQ ID No. 3) were joined with a linker having a DNA sequence of SEQ ID No. 5 by PCR.

The DNA sequence of the P IFNα (SEQ ID No. 1) was amplified by PCR with the following PCR primers.

```
Forward primer (IFN-F2):
                                    (SEQ ID NO: 15)
5'-GCGATATCATGGCCCCAACCTC-3'
      EcoRV Reverse primer (IFN-R2):
                                    (SEQ ID NO: 16)
5'-CGGGATCCACCTGAGCCACCCAGGTTTCTGGAGG-3'
      BamHI
```

The doubly underlined nucleotides are one partial sequence of the linker.

The DNA sequence of the P IgG Fc (SEQ ID No. 3) was amplified by PCR with the following PCR primers.

```
Forward primer (IgG-F2):
                                    (SEQ ID NO: 17)
5'-CGGGATCCGGTGGAGGCGGAAGCGGCGGTGGAGGATCAGGAACA
      BamHI

AAGA-3'

Reverse primer (IgG-R):
                                    (SEQ ID NO: 14)
5'-CCCAAGCTTTTTACCCGGAGTC-3'
      HindIII
```

The doubly underlined nucleotides are the other partial sequence of the linker.

PCR mixtures containing 10 µl of pET20b-IFNα or pET20b-IgG-Fc, 5 µl of 10×PCR buffer, 8 µl of 1.25 mM dNTP, 1 µl of forward primer, 1 µl of reverse primer, 33 µl autoclaved water, and 1 µl of Taq polymerase were placed in a GeneAmp® PCR System 2400 reactor (Applied Biosystems). After inactivating the plasmids at 95° C. for 5 minutes, the plasmids were amplified by Taq polymerase with 30 cycles of 95° C. for 1 minute, 55° C. for 30 seconds, 72° C. for 30 seconds, followed by a 72° C. for 5 minutes incubation.

An EcoRV site at the 5' end and a BamHI site at the 3' end of the porcine IFN α gene were created by PCR. A BamHI site at the 5' end and a HindIII site at the 3' end of the P IgG Fc were created by PCR. The PCR products were gel-purified and subcloned into pET20b expression vectors by the methods described in Example 1. Then DNA sequence was confirmed by sequencing. The P IFN-Fc has a DNA sequence of SEQ ID No. 7 and an amino acid sequence of SEQ ID No. 8. The plasmid containing the DNA sequence of the porcine recombinant fusion IFNα (P IFNα-Fc) is named pET20b-INFα-Fc.

EXAMPLE 4

Subcloning of Polynucleotide Sequence Encoding Porcine Recombinant Fusion IFN (P IFN-Fc)

Since mammalian cells are able to perform the most comprehensive post-translational modifications and to correctly fold foreign proteins, the DNA sequence of the porcine recombinant fusion IFN (P IFN-Fc) constructed in Example 3 was modified by PCR and then subcloned into pSecTag2(B) mammalian expression vectors. The DNA sequence of the modified porcine recombinant fusion IFN (mP IFN-Fc) is more suitable for being expressed in eukaryotic expression systems than the unmodified sequence.

The plasmid pET20b-IFNα-Fc constructed in Example 3 was used as PCR template. The P IFNα-Fc was amplified by PCR method described in Example 3 with the following PCR primers.

```
Forward primer (IFN-Fc-F):
                                          (SEQ ID NO: 18)
5'-CCCAAGCTTGCCGCCGCCATGGCCCCAACCTCAGCCTTC-3'
      HindIII Reverse primer (IFN-Fc-R):
                                          (SEQ ID NO: 19)
5'-CGGAATTCCTCAGTGGTGGTGGTGGTGGTGTTTGCCGGGGGTCT
      EcoRI

TGAAG-3'
```

A HindIII site at the 5' end and an EcoRI site at the 3' end of the modified porcine recombinant fusion IFN (mP IFN-Fc) were created by PCR. The PCR products were gel-purified and subcloned into pSecTag2(B) expression vectors by the methods described in Example 1. Then DNA sequence was confirmed by sequencing. The mP IFN-Fc has a DNA sequence of SEQ ID No. 9 and an amino acid sequence of SEQ ID No. 8. The plasmid containing the DNA sequence of the mP IFN-Fc is named pSecTag2(B)-IFNα-Fc.

EXAMPLE 5

Expression of Porcine Recombinant Fusion IFN (P IFN-Fc)

The plasmid pSecTag2(B)-IFNα-Fc constructed in Example 4 was transfected into CHO cells. First, 4 μg of pSecTag2(B)-IFNα-Fc DNA was diluted into VP serum-free medim (Invitrogen) without antibiotics, and 4 μg of Lipofectamine (Invitrogen) was diluted into VP serum-free medim (Invitrogen) without antibiotics and then incubated at room temperature for 5 minutes. Next, the diluted plasmid DNA was mixed with the diluted Lipofectamine, and the mixture was incubated at 37° C. for 20 minutes. Then the mixture was evenly added to CHO cells that were cultured overnight, and the CHO cells with the mixture were further incubated at 37° C. in a 5% $CO_2$ incubator for 6 hours. After incubation, the mixture was removed, and F12 medium containing 10% fetal bovine serum (FBS) was added to the CHO cells. The CHO cells were then cultivated at 37° C. in a 5% $CO_2$ incubator for 48 hours.

The transfected CHO cells were then washed twice with phosphate buffered saline (PBS), dissociated with 0.125% trypsin, and then cultivated at 37° C., 5% $CO_2$ in F12 medium with 10% FBS, 100 units/ml penicillin, 100 units/ml streptomycin, and 700 μg/ml Zeocin to select cells comprising the modified porcine recombinant fusion IFN (mP IFN-Fc) gene. The selective medium was replenished every 3 to 4 days until 10 to 20% of cells survived. The surviving cells were cultivated in F12 medium with 10% FBS and 50 μg/ml Zeocin until the cells grew to near confluence. Expression of the porcine recombinant fusion IFN (P IFN-Fc) from the selective cells was then detected by immunofluorescent assay (IFA), enzyme-linked immunosorbent assay (ELISA), and Western blot with proper antibodies.

1. Bioassay of the Porcine Recombinant Fusion IFN (P IFN-Fc) by IFA

Sample cells were seeded in a 24-well culture plate ($1 \times 10^5$ cells/well) and grew to 80 to 90% confluence. The sample cells were then washed twice with PBS and fixed with 80% acetone for 30 minutes at 4° C. Then, acetone was discarded, and the cells were washed three times with PBS. After that, the cells were incubated with rabbit anti Porcine IgG-Fluorescein isothiocyanate (FITC) antibody (300 μl/well) (1:1000 dilution in PBS) for 30 minutes at 37° C. Then, the antiserum was discarded, and the cells were washed three times with PBS and finally mounted in 250 μl PBS for fluorescent microscopic examination.

Fluorescent signals were detected in CHO cells that was transfected with pSecTag2(B)-IFNα-Fc and then selected by zeocin. No fluorescent signal was detected in CHO cells that was transfected with pSecTag2(B) and then selected by zeocin.

2. Bioassay of the Porcine Recombinant Fusion IFN (P IFN-Fc) by ELISA

Sample cells were cultivated in F-12 medium with 10% FBS for 72 hours, and then the supernatant was collected and diluted two-fold serially with ELISA coating buffer (0.1 M $NaHCO_3$ and 0.1 M $Na_2CO_3$, pH9.6). 100 μl of each diluted sample was added to an ELISA plate (NUNC) and placed at 4° C. for 24 hours. After that, the diluted supernatant was removed, and the ELISA plate was washed three times with ELISA washing buffer (0.9% NaCl, 0.1% Tween20). Blocking buffer (1% BSA in ELISA washing buffer) was added to the ELISA plate (100 μl/well), and the plate was incubated at room temperature for 1 hour to prevent non-specific binding of proteins. Then the blocking buffer was removed and the ELISA plate was washed three times with ELISA washing buffer. Mouse anti IFNα monoclonal antibody (SANTA CRUZ) was diluted five hundred-fold (1:500) with ELISA washing buffer containing 1% BSA and then added to the ELISA plate (100 μl/well). After incubated at room temperature for 1 hour, the ELISA plate was washed six times with ELISA washing buffer. Goat anti mouse secondary antibody (KPL) conjugated to horseradish peroxidase (HRP) was diluted one thousand-fold (1:1000) with ELISA washing buffer containing 1% BSA and then added to the ELISA plate (100 μl/well). After incubating for 1 hour at 37° C., the plate was washed six times with PBS. For visualization of results, 3,3',5, 5'-tetramethylbenzidine (TMB) (KPL) was added to the wells. After incubation for 10 minutes, the absorbance of the signals was read using an ELISA reader set at 650 nm.

FIG. 1 shows the results of bioassay of the porcine recombinant fusion IFN (P IFN-Fc) by ELISA test. Porcine recombinant fusion IFN (P IFN-Fc) was detected in secretions from CHO cells that was transfected with pSecTag2(B)-IFNα-Fc. Even diluted 128-fold, the recombinant fusion IFN is still detectable. No porcine recombinant fusion IFN (P IFN-Fc) was detected in secretions from CHO cells that was transfected with pSecTag2(B).

3. Bioassay of the Porcine Recombinant Fusion IFN (P IFN-Fc) by Western Blot

Sample cells were cultivated in F-12 medium with 10% FBS for 72 hours, and then the supernatant was collected and analyzed by sodium dodecyl sulfate-polyacrylamide gel electrophoresis (SDS-PAGE). For protein immunoblotting, following electrophoresis, proteins were transferred to a PVDF membrane. The resulting membrane was blocked with 5% skim milk in TBST (10 mM Tris-HCl pH 8.0, 150 mM NaCl, 0.3% Tween 20) at 4° C. for 16 to 24 hours to prevent non-specific binding of proteins and then washed 3 times with TBST. The membrane was then incubated with mouse anti IFNα monoclonal antibody (SANTA CRUZ) (1:500 dilution in TBST containing 0.5% skin milk) at room temperature for 1 hour. The blots were then washed 6 times with TBST and incubated with alkaline phosphatase (AP) conjugated goat anti-mouse IgG monoclonal antibody (1:2000 dilution in TBST containing 0.5% skin milk) at room temperature for 1 hour. The blots were then washed 6 times with TBST. The bands were detected using nitro blue tetrazolium (NBT)/5-bromo-4-chloro-3-indolyl-phosphate (BCIP) substrate for 5 minutes and then washed with water to stop the reaction. In addition, the porcine recombinant fusion IFN (P IFN-Fc) was also detected using alkaline phosphatase (AP) conjugated goat anti-porcine IgG antibody (KPL) and using alkaline phosphatase (AP) conjugated mouse anti 6×His monoclonal antibody (invitrogen).

Figure 2:
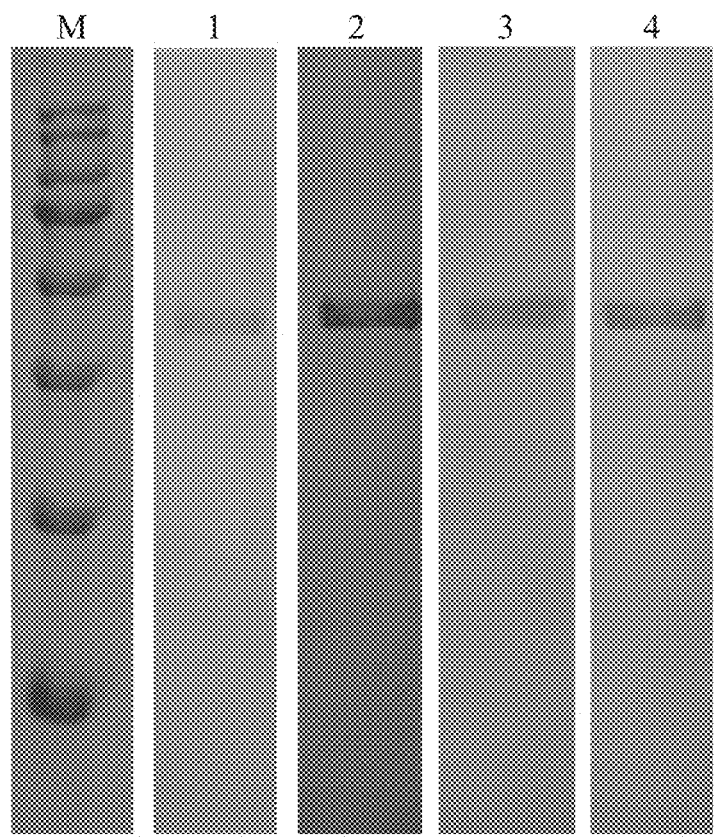
FIG. 2 shows Western blots of protein expressed in CHO cells comprising a DNA sequence encoding the recombinant fusion IFN for animals according to one embodiment of the present invention. M: protein marker; lane 1: SDS-PAGE analysis of the protein; lane 2: Western blot detected using mouse anti-IFNα monoclonal antibody; lane 3: Western blot detected using mouse anti-His monoclonal antibody; lane 4: Western blot detected using goat anti-porcine IgG antibody.

FIG. 2 shows results of Western blots of protein expressed in CHO cells that was transfected with pSecTag2(B)-IFNα-Fc. Porcine recombinant fusion IFN (P IFN-Fc) was detected by mouse anti IFNα monoclonal antibody (lane 2), mouse anti 6×His monoclonal antibody (lane 3), and goat anti-porcine IgG antibody (lane 4). The results show that CHO cells that was transfected with pSecTag2(B)-IFNα-Fc secrete the Porcine recombinant fusion IFN (P IFN-Fc).

EXAMPLE 6

Small-Scale and Large-Scale Production of Porcine Recombinant Fusion IFN (P IFN-Fc)

1. Small-Scale Production of Porcine Recombinant Fusion IFN (P IFN-Fc)

CHO cells comprising pSecTag2(B)-IFNα-Fc was seeded at a density of $2 \times 10^6$ cells in a 25 cm$^2$ cell culture flask and cultivated in F12 medium with 10% FBS, 100 units/ml penicillin, and 100 units/ml streptomycin for 24 hours. The medium was then removed. The cells were washed with PBS and then cultivated in CHO-S-SFM II serum-free medium (GIBCO) with 100 units/ml penicillin and 100 units/ml streptomycin. Supernatant was collected and fresh serum-free medium containing penicillin and streptomycin was added every 24, 48, and 72 hours respectively. The supernatant containing the porcine recombinant fusion IFN (P IFN-Fc) was centrifuged (1,000 rpm) for 10 minutes to remove cells and cell debris.

Concentration of the porcine recombinant fusion IFN (P IFN-Fc) was calculated by evaluating its antiviral activity against porcine reproductive and respiratory syndrome virus (PRRSV). The porcine recombinant fusion IFN (P IFN-Fc) was diluted serially (10, 20, 40, 80, 160, 320, 640, 1280, and 2560-folds) with minimum essential media (MEM medium) containing 1% FBS, 100 units/ml penicillin, and 100 units/ml streptomycin. MARC-145 cells were seeded at a density of $1.5 \times 10^4$ cells/well in 96-well cell culture plates and cultivated at 37° C., 5% CO$_2$ for 16 to 24 hours. After the culture medium was removed, the cells were treated with the diluted porcine recombinant fusion IFN (P IFN-Fc) (100 μl/well, n=4), and then cultivated at 37° C., 5% CO$_2$ for 24 hours. After the diluted samples were removed, the cells were infected with PRRS virus (100 TCID$_{50}$/100 μl) and then cultivated at 37° C., 5% CO$_2$ for about 120 hours until 90% of cells showing cytopathic effects (CPE). Then cells were used to evaluate the antiviral activity of the porcine recombinant fusion IFN (P IFN-Fc).

Cell suspension was removed, and the cells were washed twice with PBS and then fixed on the plate with 80% acetone (−20° C., 100 μl/well) at 4° C. for 30 minutes. After acetone was removed, the cells were washed 3 times with PBS and stained with 1% methylrosaniline chloride for 20 minutes. After that, the cells were washed 5 times with distilled water, and then 100% ethanol was added to dissolve methylrosaniline chloride. 10 minutes later, the absorbance of the signals was read using an ELISA reader set at 550 nm. Concentration of the porcine recombinant fusion IFN (P IFN-Fc) was calculated by the following formulas.

$$\frac{OD\text{maximum} + OD\text{minimum}}{2} = OD50\% \quad \text{Formula 1}$$

where OD maximum is absorbancy of uninfected cell monolayers treated or untreated with IFN (protection 100%), and OD minimum is absorbancy of the infected non-protected cell monolayer (protection zero).

$$IFN \text{ titer (U ml}^{-1}) = T_n + \left[(T_{n+1} - T_n) \times \frac{(OD_n - OD50\%)}{(OD_n - OD_{n+1})}\right] \quad \text{Formula 2}$$

where $T_n$ is reciprocal of the IFN dilution corresponding to OD immediately higher than OD50%, $T_{n+1}$ is reciprocal of the IFN dilution corresponding to OD immediately lower than the OD50%, $OD_n$ is the absorbancy values immediately higher than OD50%, and $OD_{n+1}$ is the absorbancy values immediately lower than OD50%.

Table 1 shows the concentration of the porcine recombinant fusion IFN (P IFN-Fc) produced by the small-scale production method described above. The results show that the porcine recombinant fusion IFN (P IFN-Fc) possesses antiviral activity against PRRSV.

TABLE 1

Concentration (IU/ml) of the porcine recombinant fusion IFN (P IFN-Fc) produced in 25 cm$^2$ cell culture flasks.

| Cultivation Time (Hours) | Number of Collecting Sample | | | | | |
|---|---|---|---|---|---|---|
| | 1$^{st}$ time (IU/ml) | 2$^{nd}$ time (IU/ml) | 3$^{rd}$ time (IU/ml) | 4$^{th}$ time (IU/ml) | 5$^{th}$ time (IU/ml) | 6$^{th}$ time (IU/ml) |
| 24 | 189.59 | 249.21 | 1444.77 | 1645.70 | 511.23 | 1372.38 |
| 48 | 215.13 | 669.09 | 246.92 | 278.10 | 686.99 | 3434.07 |
| 72 | 643.38 | 1194.90 | 964.14 | 2539.12 | 1931.84 | 3147.87 |

Table 2 shows the amount of the porcine recombinant fusion IFN (P IFN-Fc) produced by the small-scale production method, which was calculated by multiplying the concentration of the porcine recombinant fusion IFN (P IFN-Fc) by the volume of a 25 cm$^2$ cell culture flask (5 ml).

TABLE 2

The amount of the porcine recombinant fusion IFN (P IFN-Fc) produced in a 25 cm$^2$ cell culture flask (IU).

| Cultivation Time (Hours) | Number of Collecting Sample | | | | | |
|---|---|---|---|---|---|---|
| | 1$^{st}$ time (IU/ml) | 2$^{nd}$ time (IU/ml) | 3$^{rd}$ time (IU/ml) | 4$^{th}$ time (IU/ml) | 5$^{th}$ time (IU/ml) | 6$^{th}$ time (IU/ml) |
| 24 | 947.95 | 1246.05 | 7223.85 | 8228.5 | 2556.15 | 6861.9 |
| 48 | 1075.65 | 3345.45 | 1234.6 | 1390.5 | 3434.95 | 17170.35 |
| 72 | 3216.9 | 5974.5 | 4820.7 | 12695.6 | 9659.2 | 15739.35 |

2. Large-Scale Production of Porcine Recombinant Fusion IFN (P IFN-Fc)

CHO cells comprising pSecTag2(B)-IFNα-Fc was first cultivated in a 175 cm² cell culture flask. After a monolayer of the cells was formed, the cells were dissociated with 0.125% trypsin and suspended with F12 medium containing 10% FBS, 100 units/ml penicillin, and 100 units/ml streptomycin for cell counting. Then, the cells were seeded in roller bottles at the concentrations of $6.8 \times 10^7$ cells/bottle and $8 \times 10^7$ cells/bottle respectively, and cultivated in 200 ml of F12 medium containing 10% FBS at 37° C., 0.167 rpm. Twenty four hours later, the cells were washed with PBS and cultivated in CHO-S-SFM II serum-free medium (Invitrogen) containing 100 units/ml penicillin and 100 units/ml streptomycin. Supernatant was collected and fresh serum-free medium containing penicillin and streptomycin was added every 72 hours for 6 times. The supernatant comprising the porcine recombinant fusion IFN (P IFN-Fc) was centrifuged (1,000 rpm) for 10 minutes to remove cells and cell debris. Concentration of the porcine recombinant fusion IFN (P IFN-Fc) was calculated by evaluating its antiviral activity against PRRSV with the method described above.

Table 3 shows the concentration of the porcine recombinant fusion IFN (P IFN-Fc) produced by roller bottles. The results show that the porcine recombinant fusion IFN (P IFN-Fc) produced by roller bottles possesses higher antiviral activity against PRRSV than the IFN (P IFN-Fc) produced by 25 cm² cell culture flasks.

TABLE 3

Concentration (IU/ml) of the porcine recombinant fusion IFN (P IFN-Fc) produced in roller bottles.

| Cell number | Number of Collecting Sample | | | | | |
| --- | --- | --- | --- | --- | --- | --- |
| | 1st time (IU/ml) | 2nd time (IU/ml) | 3rd time (IU/ml) | 4th time (IU/ml) | 5th time (IU/ml) | 6th time (IU/ml) |
| $6.8 \times 10^7$ cells | 4612.2 | 20771.0 | 43389.8 | 78104.7 | 68974.8 | 83194.7 |
| $8.0 \times 10^7$ cells | 10123.6 | 27704.9 | 33387.6 | 43419.6 | 36846.3 | 48641.7 |

Table 4 shows the amount of the porcine recombinant fusion IFN (P IFN-Fc) produced by the large-scale production method.

TABLE 4

The amount of the porcine recombinant fusion IFN (P IFN-Fc) produced in a roller bottle (IU).

| Cell number | Number of Collecting Sample | | | | | |
| --- | --- | --- | --- | --- | --- | --- |
| | 1st time (IU/ml) | 2nd time (IU/ml) | 3rd time (IU/ml) | 4th time (IU/ml) | 5th time (IU/ml) | 6th time (IU/ml) |
| $6.8 \times 10^7$ cells | 922440 | 4154200 | 8677960 | 15620940 | 13794960 | 16638940 |
| $8.0 \times 10^7$ cells | 2024720 | 5540980 | 6677520 | 8683920 | 7369260 | 9728340 |

EXAMPLE 7

Comparison of Antiviral Activities Against PRRSV of the Porcine Recombinant Fusion IFN (P IFN-Fc) and a Porcine IFN (P IFN)

MARC-145 cells were cultivated at a density of $1.5 \times 10^4$ cells/well in 96-well cell culture plates at 37° C., 5% $CO_2$ for 16 to 24 hours. After the culture medium was removed, the cells were treated with the porcine recombinant fusion IFN (P IFN-Fc) or a porcine IFN encoding an amino acid sequence of SEQ ID No. 2 (P IFN) for 16 to 24 hours. After the two types of IFN were removed, the cells were infected with PRRS virus (100 $TCID_{50}$/100 μl) and then cultivated at 37° C., 5% $CO_2$ for 4 to 5 days. Then cell viabilities were analyzed by MTT method.

Figure 3:
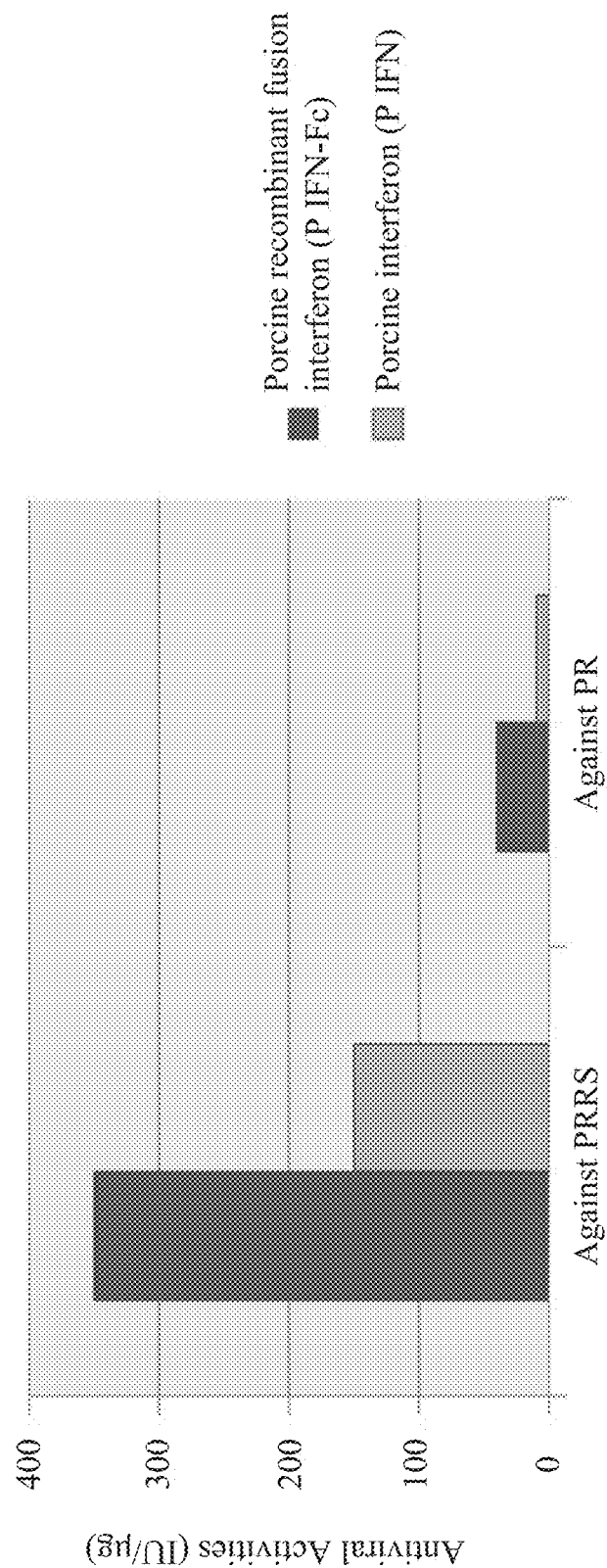
FIG. 3 shows the results of antiviral infection assays for the recombinant fusion IFN for animals according to one embodiment of the present invention (P IFN-Fc) and porcine IFN (P IFN) in Marc-145 cells with PRRSV challenges and in ST cells with PR challenges.

Table 5 and FIG. 3 show the results of the assays of antiviral activity against PRRSV of the porcine recombinant fusion IFN (P IFN-Fc) and the porcine IFN (P IFN). The results show that the porcine recombinant fusion IFN (P IFN-Fc) possesses a higher antiviral activity against PRRSV than the porcine IFN (P IFN).

TABLE 5

Comparison of antiviral activities against PRRSV of the porcine recombinant fusion IFN (P IFN-Fc) and the porcine IFN (P IFN).

| Treatment | Antiviral Activities Against PRRSV (IU/μg) |
| --- | --- |
| P IFN-Fc | 350 |
| P IFN | 150 |

EXAMPLE 8

Comparison of Antiviral Activities Against PRV of the Porcine Recombinant Fusion IFN (P IFN-Fc) and a Porcine IFN (P IFN)

ST cells were cultivated at a density of $1.5 \times 10^4$ cells/well in 96-well cell culture plates at 37° C., 5% $CO_2$ for 16 to 24 hours. After the culture medium was removed, the cells were treated with the porcine recombinant fusion IFN (P IFN-Fc) or the porcine IFN encoding an amino acid sequence of SEQ ID No. 2 (P IFN) for 16 to 24 hours. After the two types of IFN were removed, the cells were infected with PR virus (1 $TCID_{50}$/100 μl) and then cultivated at 37° C., 5% $CO_2$ for 4 to 5 days. Then cell viabilities were analyzed by MTT method.

Table 6 and FIG. 3 show the results of the assays of antiviral activity against PRV of the porcine recombinant fusion IFN (P IFN-Fc) and the porcine IFN (P IFN). The results show that the porcine recombinant fusion IFN (P IFN-Fc) possesses a higher antiviral activity against PRV than the porcine IFN (P IFN).

TABLE 6

Comparison of antiviral activities against PRV of the porcine recombinant fusion IFN (P IFN-Fc) and the porcine IFN (P IFN).

| Treatment | Antiviral Activities Against PRRSV (IU/μg) |
| --- | --- |
| P IFN-Fc | 40 |
| P IFN | 9.6 |

Based on the results of the Examples above, the recombinant fusion IFN for animals of the present invention possesses higher antiviral activities against both RNA virus and DNA virus than an animal IFN.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments are chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, to promote the progress in science and the useful arts, the scope of the present invention is disclosed and is intended to be limited only defined by the scope of the appended claims, rather than the foregoing description and the exemplary embodiments described therein.

What is claimed is:

1. A polynucleotide encoding a recombinant fusion interferon, comprising the polynucleotide sequence of SEQ ID NO: 7 or 9, wherein the encoded recombinant fusion interferon comprises the amino acid sequence of SEQ ID NO: 2 corresponding to a porcine interferon and the amino acid sequence of SEQ ID NO: 4 corresponding to a porcine immunoglobulin Fc fragment, and the recombinant fusion interferon has a greater antivirus activity than a non-fusion porcine interferon for inhibition of a porcine virus.

2. The polynucleotide of claim 1, wherein the porcine virus is porcine reproductive and respiratory syndrome virus (PRRSV).

3. The polynucleotide of claim 1, wherein the porcine virus is pseudorabies virus (PRV).

4. A method for producing a recombinant fusion interferon, comprising:
   providing mammalian cells having a vector for expression, wherein the vector comprises the polynucleotide of claim 1 inserted therein;
   cultivating the mammalian cells in serum-containing medium;
   replacing the serum-containing medium with serum-free medium after the cells growing stably; and
   collecting the serum-free medium and adding new serum-free medium to the cells every 1 to 5 days.

5. The method of claim 4, wherein the serum-containing medium comprises about 0.1 to 10% (v/v) of serum.

* * * * *

SEQUENCE LISTING

```
<160> NUMBER OF SEQ ID NOS: 19

<210> SEQ ID NO 1
<211> LENGTH: 543
<212> TYPE: DNA
<213> ORGANISM: Sus scrofa

<400> SEQUENCE: 1
atggccccaa cctcagcctt cctcacagcc ctggtgctac tcagctgcaa tgccatctac      60
tctctgggct gtgacctgcc tcagacccac agcctggctc acaccagggc cctgaggctc     120
ctggcacaaa tgaggagaat ctcccccttc tcctgcctgg accacagaag ggactttgga     180
ttcccccaag aggccttggg gggcaaccag gtccagaagg ctcaagccat ggctctggtg     240
catgagatgc tccagcagac cttccagctc ttcagcacag agggctcggc tgctgcctgg     300
gatgagagcc tcctgcacca gttctgcact ggactggatc agcagctcag ggacctggaa     360
gcctgtgtca tgcaggaggc ggggctggaa gggacccccc tgctggagga ggactccatc     420
ctggctgtga ggaaatactt ccacagactc accctctatc tgcaagagaa gagctacagc     480
ccctgtgcct gggagatcgt cagagcagaa gtcatgagag ccttctcttc ctccagaaac     540
ctg                                                                   543

<210> SEQ ID NO 2
<211> LENGTH: 181
<212> TYPE: PRT
<213> ORGANISM: Sus scrofa

<400> SEQUENCE: 2

Met Ala Pro Thr Ser Ala Phe Leu Thr Ala Leu Val Leu Leu Ser Cys
1               5                   10                  15

Asn Ala Ile Tyr Ser Leu Gly Cys Asp Leu Pro Gln Thr His Ser Leu
            20                  25                  30

Ala His Thr Arg Ala Leu Arg Leu Leu Ala Gln Met Arg Arg Ile Ser
        35                  40                  45

Pro Phe Ser Cys Leu Asp His Arg Arg Asp Phe Gly Phe Pro Gln Glu
    50                  55                  60

Ala Leu Gly Gly Asn Gln Val Gln Lys Ala Gln Ala Met Ala Leu Val
65                  70                  75                  80

His Glu Met Leu Gln Gln Thr Phe Gln Leu Phe Ser Thr Glu Gly Ser
                85                  90                  95

Ala Ala Ala Trp Asp Glu Ser Leu Leu His Gln Phe Cys Thr Gly Leu
            100                 105                 110

Asp Gln Gln Leu Arg Asp Leu Glu Ala Cys Val Met Gln Glu Ala Gly
        115                 120                 125

Leu Glu Gly Thr Pro Leu Leu Glu Glu Asp Ser Ile Leu Ala Val Arg
```

```
                    130                 135                 140
Lys Tyr Phe His Arg Leu Thr Leu Tyr Leu Gln Glu Lys Ser Tyr Ser
145                 150                 155                 160

Pro Cys Ala Trp Glu Ile Val Arg Ala Glu Val Met Arg Ala Phe Ser
                165                 170                 175

Ser Ser Arg Asn Leu
            180

<210> SEQ ID NO 3
<211> LENGTH: 690
<212> TYPE: DNA
<213> ORGANISM: Sus scrofa

<400> SEQUENCE: 3
ggaacaaaga ccaaaccacc atgtcccata tgcccagcct gtgaagggcc cgggccctcg     60
gccttcatct tccctccaaa acccaaggac accctcatga tctcccggac ccccaaggtc    120
acgtgcgtgg tggtagatgt gagccaggag aacccggagg tccagttctc ctggtacgtg    180
gacggcgtag aggtgcacac ggcccagacg aggccaaagg aggagcagtt caacagcacc    240
taccgcgtgg tcagcgtcct gcccatccag caccaggact ggctgaacgg gaaggagttc    300
aagtgcaagg tcaacaacaa agacctccca gcccccatca aaggatcat ctccaaggcc     360 aaagggcaga cccgggagcc gcaggtgtac accctgcccc cacccaccga ggagctgtcc    420
aggagcaaag tcacgctaac ctgcctggtc actggcttct acccacctga catcgatgtc    480
gagtggcaaa gaaacggaca gccggagcca gagggcaatt accgcaccac cccgccccag    540
caggacgtgg acgggaccta cttcctgtac agcaagctcg cggtggacaa ggccagctgg    600
cagcgtggag acacattcca gtgtgcggtg atgcacgagg ctctgcacaa ccactacacc    660
cagaagtcca tcttcaagac tccgggtaaa                                    690

<210> SEQ ID NO 4
<211> LENGTH: 230
<212> TYPE: PRT
<213> ORGANISM: Sus scrofa

<400> SEQUENCE: 4

Gly Thr Lys Thr Lys Pro Pro Cys Pro Ile Cys Pro Ala Cys Glu Gly
1               5                   10                  15

Pro Gly Pro Ser Ala Phe Ile Phe Pro Pro Lys Pro Lys Asp Thr Leu
                20                  25                  30

Met Ile Ser Arg Thr Pro Lys Val Thr Cys Val Val Asp Val Ser
            35                  40                  45

Gln Glu Asn Pro Glu Val Gln Phe Ser Trp Tyr Val Asp Gly Val Glu
        50                  55                  60

Val His Thr Ala Gln Thr Arg Pro Lys Glu Glu Gln Phe Asn Ser Thr
65                  70                  75                  80

Tyr Arg Val Val Ser Val Leu Pro Ile Gln His Gln Asp Trp Leu Asn
                85                  90                  95

Gly Lys Glu Phe Lys Cys Lys Val Asn Asn Lys Asp Leu Pro Ala Pro
            100                 105                 110

Ile Thr Arg Ile Ile Ser Lys Ala Lys Gly Gln Thr Arg Glu Pro Gln
        115                 120                 125

Val Tyr Thr Leu Pro Pro Thr Glu Glu Leu Ser Arg Ser Lys Val
    130                 135                 140

Thr Leu Thr Cys Leu Val Thr Gly Phe Tyr Pro Pro Asp Ile Asp Val
```

```
                145                 150                 155                 160
Glu Trp Gln Arg Asn Gly Gln Pro Glu Pro Glu Gly Asn Tyr Arg Thr
                    165                 170                 175

Thr Pro Pro Gln Gln Asp Val Asp Gly Thr Tyr Phe Leu Tyr Ser Lys
                180                 185                 190

Leu Ala Val Asp Lys Ala Ser Trp Gln Arg Gly Asp Thr Phe Gln Cys
            195                 200                 205

Ala Val Met His Glu Ala Leu His Asn His Tyr Thr Gln Lys Ser Ile
        210                 215                 220

Phe Lys Thr Pro Gly Lys
225                 230

<210> SEQ ID NO 5
<211> LENGTH: 48
<212> TYPE: DNA
<213> ORGANISM: Artificial Sequence
<220> FEATURE:
<223> OTHER INFORMATION: DNA sequence of a linker of interferon and IgG
      Fc fragement

<400> SEQUENCE: 5
ggtggctcag gtggatccgg tggaggcgga agcggcggtg aggatca                    48

<210> SEQ ID NO 6
<211> LENGTH: 16
<212> TYPE: PRT
<213> ORGANISM: Artificial Sequence
<220> FEATURE:
<223> OTHER INFORMATION: Amino acid sequence of a linker of interferon
      and IgG Fc fragement

<400> SEQUENCE: 6

Gly Gly Ser Gly Gly Ser Gly Gly Gly Gly Ser Gly Gly Gly Gly Ser
1               5                   10                  15

<210> SEQ ID NO 7
<211> LENGTH: 1281
<212> TYPE: DNA
<213> ORGANISM: Artificial Sequence
<220> FEATURE:
<223> OTHER INFORMATION: DNA sequence of interferon recombinant protein

<400> SEQUENCE: 7
atggccccaa cctcagcctt cctcacagcc ctggtgctac tcagctgcaa tgccatctac     60
tctctgggct gtgacctgcc tcagacccac agcctggctc acaccagggc cctgaggctc    120
ctggcacaaa tgaggagaat ctccccttc tcctgcctgg accacagaag ggactttgga    180
ttcccccaag aggccttggg gggcaaccag gtccagaagg ctcaagccat ggctctggtg    240
catgagatgc tccagcagac cttccagctc ttcagcacag agggctcggc tgctgcctgg    300
gatgagagcc tcctgcacca gttctgcact ggactggatc agcagctcag ggacctggaa    360
gcctgtgtca tgcaggaggc ggggctggaa gggacccccc tgctggagga ggactccatc    420
ctggctgtga ggaaatactt ccacagactc accctctatc tgcaagagaa gagctacagc    480
ccctgtgcct gggagatcgt cagagcagaa gtcatgagag ccttctcttc tccagaaac    540 ctgggtggct caggtggatc cggtggaggc ggaagcggcg gtgaggatca ggaacaaag    600 accaaaccac catgtcccat gcccagctg tgtgaaggc ccgggccctc ggccttcatc    660
ttccctccaa aacccaagga caccctcatg atctccccgga ccccaaggt cacgtgcgtg    720 gtggtagatg tgagccagga gaacccggag gtccagttct cctggtacgt ggacggcgta    780
```

-continued

```
gaggtgcaca cggcccagac gaggccaaag gaggagcagt tcaacagcac ctaccgcgtg    840
gtcagcgtcc tgcccatcca gcaccaggac tggctgaacg ggaaggagtt caagtgcaag    900
gtcaacaaca agaccctccc agcccccatc acaaggatca tctccaaggc caagggcag     960 acccgggagc cgcaggtgta caccctgccc ccacccaccg aggagctgtc caggagcaaa   1020
gtcacgctaa cctgcctggt cactggcttc tacccacctg acatcgatgt cgagtggcaa   1080
agaaacggac agccggagcc agagggcaat taccgcacca ccccgcccca gcaggacgtg   1140
gacgggacct acttcctgta cagcaagctc gcggtggaca aggccagctg gcagcgtgga   1200
gacacattcc agtgtgcggt gatgcacgag gctctgcaca accactacac ccagaagtcc   1260
atcttcaaga ctccgggtaa a                                             1281
```

<210> SEQ ID NO 8
<211> LENGTH: 427
<212> TYPE: PRT
<213> ORGANISM: Artificial Sequence
<220> FEATURE:
<223> OTHER INFORMATION: Amino acid sequence of interferon recombinant protein

<400> SEQUENCE: 8

```
Met Ala Pro Thr Ser Ala Phe Leu Thr Ala Leu Val Leu Leu Ser Cys
1               5                   10                  15

Asn Ala Ile Tyr Ser Leu Gly Cys Asp Leu Pro Gln Thr His Ser Leu
            20                  25                  30

Ala His Thr Arg Ala Leu Arg Leu Leu Ala Gln Met Arg Arg Ile Ser
        35                  40                  45

Pro Phe Ser Cys Leu Asp His Arg Arg Asp Phe Gly Phe Pro Gln Glu
    50                  55                  60

Ala Leu Gly Gly Asn Gln Val Gln Lys Ala Gln Ala Met Ala Leu Val
65                  70                  75                  80

His Glu Met Leu Gln Gln Thr Phe Gln Leu Phe Ser Thr Glu Gly Ser
                85                  90                  95

Ala Ala Ala Trp Asp Glu Ser Leu Leu His Gln Phe Cys Thr Gly Leu
            100                 105                 110

Asp Gln Gln Leu Arg Asp Leu Glu Ala Cys Val Met Gln Glu Ala Gly
        115                 120                 125

Leu Glu Gly Thr Pro Leu Leu Glu Glu Asp Ser Ile Leu Ala Val Arg
    130                 135                 140

Lys Tyr Phe His Arg Leu Thr Leu Tyr Leu Gln Glu Lys Ser Tyr Ser
145                 150                 155                 160

Pro Cys Ala Trp Glu Ile Val Arg Ala Glu Val Met Arg Ala Phe Ser
                165                 170                 175

Ser Ser Arg Asn Leu Gly Gly Ser Gly Gly Ser Gly Gly Gly Gly Ser
            180                 185                 190

Gly Gly Gly Gly Ser Gly Thr Lys Thr Lys Pro Pro Cys Pro Ile Cys
        195                 200                 205

Pro Ala Cys Glu Gly Pro Gly Pro Ser Ala Phe Ile Phe Pro Pro Lys
    210                 215                 220

Pro Lys Asp Thr Leu Met Ile Ser Arg Thr Pro Lys Val Thr Cys Val
225                 230                 235                 240

Val Val Asp Val Ser Gln Glu Asn Pro Glu Val Gln Phe Ser Trp Tyr
                245                 250                 255

Val Asp Gly Val Glu Val His Thr Ala Gln Thr Arg Pro Lys Glu Glu
```

|  |  | 260 |  |  |  | 265 |  |  |  | 270 |  |
|---|---|---|---|---|---|---|---|---|---|---|---|

Gln Phe Asn Ser Thr Tyr Arg Val Val Ser Val Leu Pro Ile Gln His
           275                  280                  285

Gln Asp Trp Leu Asn Gly Lys Glu Phe Lys Cys Lys Val Asn Asn Lys
     290                  295                  300

Asp Leu Pro Ala Pro Ile Thr Arg Ile Ile Ser Lys Ala Lys Gly Gln
305                  310                  315                  320

Thr Arg Glu Pro Gln Val Tyr Thr Leu Pro Pro Thr Glu Leu
               325                  330                  335

Ser Arg Ser Lys Val Thr Leu Thr Cys Leu Val Thr Gly Phe Tyr Pro
     340                  345                  350

Pro Asp Ile Asp Val Glu Trp Gln Arg Asn Gly Gln Pro Glu Pro Glu
        355                  360                  365

Gly Asn Tyr Arg Thr Thr Pro Pro Gln Gln Asp Val Asp Gly Thr Tyr
          370                  375                  380

Phe Leu Tyr Ser Lys Leu Ala Val Asp Lys Ala Ser Trp Gln Arg Gly
385                  390                  395                  400

Asp Thr Phe Gln Cys Ala Val Met His Glu Ala Leu His Asn His Tyr
               405                  410                  415

Thr Gln Lys Ser Ile Phe Lys Thr Pro Gly Lys
     420                  425

```
<210> SEQ ID NO 9
<211> LENGTH: 1281
<212> TYPE: DNA
<213> ORGANISM: Artificial Sequence
<220> FEATURE:
<223> OTHER INFORMATION: DNA sequence of interferon recombinant protein

<400> SEQUENCE: 9 atggcccoaa cctccgcctt cctcacagcc ctggtgctac tcagctgcaa tgccatctac      60
tctctgggct gtgacctgcc tcagacccac agcctggctc acaccagggc cctgaggctc     120
ctggcacaaa tgaggagaat ctcccccttc tcctgcctgg accacagaag ggactttgga     180
ttcccccaag aggccttggg gggcaaccag gtccagaagg ctcaagccat ggctctggtg     240
catgagatgc tccagcagac cttccagctc ttcagcacag agggctcggc tgctgcctgg     300
gatgagagcc tcctgcacca gttctgcact ggactggatc agcagctcag ggacctggaa     360
gcctgtgtca tgcaggaggc ggggctggaa ggaccccccc tgctggagga ggactccatc     420
ctggctgtga ggaaatactt ccacagactc accctctatc tgcaagagaa gagctacagc     480
ccctgtgcct gggagatcgt cagggcagaa gtcatgagag ccttctcttc ctccagaaac     540
ctgggtggct caggtggatc cggtggaggc ggaagcggcg gtggaggatc aggaacaaag     600
accaaaccac catgtcccat gcccagcc tgtgaagggc ccggccctc ggccttcatc     660 ttccctccaa acccaagga caccctcatg atctcccgga cccccaaggt cacgtgcgtg     720
gtggtagatg tgagccagga gaacccgag gtccagttct cctggtacgt ggacggcgta     780
gaggtgcaca cggcccagac gaggccaaag gaggagcagt tcaacagcac ctaccgcgtg     840
gtcagcgtcc tgcccatcca gcaccaggac tggctgaacg gaaggagtt caagtgcaag     900 gtcaacaaca agacctcccc agcccccatc acaaggatca tctccaaggc caaagggcag     960
acccgggagc cgcaggtgta caccctgccc ccacccaccg aggagctgtc caggagcaaa    1020
gtcacgctaa cctgcctggt cactggcttc tacccacctg acatcgatgt cgagtggcaa    1080
agaaacggac agccggagcc agagggcaat taccgcacca ccccgcccca gcaggacgtg    1140
```

```
gacgggacct acttcctgta cagcaagctc gcggtggaca aggccagctg gcagcgtgga    1200
gacacattcc agtgtgcggt gatgcacgag gctctgcaca accactacac ccagaagtcc    1260
atcttcaaga ccccccggcaa a                                              1281
```

<210> SEQ ID NO 10
<211> LENGTH: 427
<212> TYPE: PRT
<213> ORGANISM: Artificial Sequence
<220> FEATURE:
<223> OTHER INFORMATION: Amino acid sequence of interferon recombinant protein

<400> SEQUENCE: 10

```
Gly Thr Lys Thr Lys Pro Pro Cys Pro Ile Cys Pro Ala Cys Glu Gly
1               5                   10                  15

Pro Gly Pro Ser Ala Phe Ile Phe Pro Pro Lys Pro Lys Asp Thr Leu
            20                  25                  30

Met Ile Ser Arg Thr Pro Lys Val Thr Cys Val Val Val Asp Val Ser
        35                  40                  45

Gln Glu Asn Pro Glu Val Gln Phe Ser Trp Tyr Val Asp Gly Val Glu
    50                  55                  60

Val His Thr Ala Gln Thr Arg Pro Lys Glu Glu Gln Phe Asn Ser Thr
65                  70                  75                  80

Tyr Arg Val Val Ser Val Leu Pro Ile Gln His Gln Asp Trp Leu Asn
                85                  90                  95

Gly Lys Glu Phe Lys Cys Lys Val Asn Asn Lys Asp Leu Pro Ala Pro
            100                 105                 110

Ile Thr Arg Ile Ile Ser Lys Ala Lys Gly Gln Thr Arg Glu Pro Gln
        115                 120                 125

Val Tyr Thr Leu Pro Pro Pro Thr Glu Glu Leu Ser Arg Ser Lys Val
    130                 135                 140

Thr Leu Thr Cys Leu Val Thr Gly Phe Tyr Pro Pro Asp Ile Asp Val
145                 150                 155                 160

Glu Trp Gln Arg Asn Gly Gln Pro Glu Pro Glu Gly Asn Tyr Arg Thr
                165                 170                 175

Thr Pro Pro Gln Gln Asp Val Asp Gly Thr Tyr Phe Leu Tyr Ser Lys
            180                 185                 190

Leu Ala Val Asp Lys Ala Ser Trp Gln Arg Gly Asp Thr Phe Gln Cys
        195                 200                 205

Ala Val Met His Glu Ala Leu His Asn His Tyr Thr Gln Lys Ser Ile
    210                 215                 220

Phe Lys Thr Pro Gly Lys Gly Ser Gly Gly Ser Gly Gly Gly Gly
225                 230                 235                 240

Ser Gly Gly Gly Gly Ser Met Ala Pro Thr Ser Ala Phe Leu Thr Ala
                245                 250                 255

Leu Val Leu Leu Ser Cys Asn Ala Ile Tyr Ser Leu Gly Cys Asp Leu
            260                 265                 270

Pro Gln Thr His Ser Leu Ala His Thr Arg Ala Leu Arg Leu Leu Ala
        275                 280                 285

Gln Met Arg Arg Ile Ser Pro Phe Ser Cys Leu Asp His Arg Arg Asp
    290                 295                 300

Phe Gly Phe Pro Gln Glu Ala Leu Gly Gly Asn Gln Val Gln Lys Ala
305                 310                 315                 320

Gln Ala Met Ala Leu Val His Glu Met Leu Gln Gln Thr Phe Gln Leu
```

```
                       325                 330                 335
Phe Ser Thr Glu Gly Ser Ala Ala Ala Trp Asp Glu Ser Leu Leu His
               340                 345                 350

Gln Phe Cys Thr Gly Leu Asp Gln Gln Leu Arg Asp Leu Glu Ala Cys
               355                 360                 365

Val Met Gln Glu Ala Gly Leu Glu Gly Thr Pro Leu Leu Glu Glu Asp
               370                 375                 380

Ser Ile Leu Ala Val Arg Lys Tyr Phe His Arg Leu Thr Leu Tyr Leu
385                 390                 395                 400

Gln Glu Lys Ser Tyr Ser Pro Cys Ala Trp Glu Ile Val Arg Ala Glu
                    405                 410                 415

Val Met Arg Ala Phe Ser Ser Ser Arg Asn Leu
                420                 425

<210> SEQ ID NO 11
<211> LENGTH: 27
<212> TYPE: DNA
<213> ORGANISM: Artificial Sequence
<220> FEATURE:
<223> OTHER INFORMATION: Forward primer for interferon

<400> SEQUENCE: 11
cccaagctta tggccccaac ctcagcc                                      27

<210> SEQ ID NO 12
<211> LENGTH: 27
<212> TYPE: DNA
<213> ORGANISM: Artificial Sequence
<220> FEATURE:
<223> OTHER INFORMATION: Reverse primer for interferon

<400> SEQUENCE: 12
ccgctcgagc aggtttctgg aggaaga                                      27

<210> SEQ ID NO 13
<211> LENGTH: 21
<212> TYPE: DNA
<213> ORGANISM: Artificial Sequence
<220> FEATURE:
<223> OTHER INFORMATION: Forward primer for IgG Fc fragement

<400> SEQUENCE: 13
cgggatccgg gaacaaagac c                                            21

<210> SEQ ID NO 14
<211> LENGTH: 22
<212> TYPE: DNA
<213> ORGANISM: Artificial Sequence
<220> FEATURE:
<223> OTHER INFORMATION: Reverse primer for IgG Fc fragement

<400> SEQUENCE: 14
cccaagcttt ttacccggag tc                                           22

<210> SEQ ID NO 15
<211> LENGTH: 22
<212> TYPE: DNA
<213> ORGANISM: Artificial Sequence
<220> FEATURE:
<223> OTHER INFORMATION: Forward primer for interferon

<400> SEQUENCE: 15
gcgatatcat ggccccaacc tc                                           22
```

```
<210> SEQ ID NO 16
<211> LENGTH: 34
<212> TYPE: DNA
<213> ORGANISM: Artificial Sequence
<220> FEATURE:
<223> OTHER INFORMATION: Reverse primer for interferon

<400> SEQUENCE: 16
cgggatccac ctgagccacc caggtttctg gagg                                   34

<210> SEQ ID NO 17
<211> LENGTH: 48
<212> TYPE: DNA
<213> ORGANISM: Artificial Sequence
<220> FEATURE:
<223> OTHER INFORMATION: Forward primer for IgG Fc fragement

<400> SEQUENCE: 17
cgggatccgg tggaggcgga agcggcggtg gaggatcagg aacaaaga                    48

<210> SEQ ID NO 18
<211> LENGTH: 39
<212> TYPE: DNA
<213> ORGANISM: Artificial Sequence
<220> FEATURE:
<223> OTHER INFORMATION: Forward primer for interferon recombinant
      protein

<400> SEQUENCE: 18
cccaagcttg ccgccgccat ggccccaacc tcagccttc                              39

<210> SEQ ID NO 19
<211> LENGTH: 48
<212> TYPE: DNA
<213> ORGANISM: Artificial Sequence
<220> FEATURE:
<223> OTHER INFORMATION: Reverse primer for interferon recombinant
      protein

<400> SEQUENCE: 19
cggaattctc agtggtggtg gtggtggtgt ttgccggggg tcttgaag                    48
```